United States Patent
Joerger et al.

(10) Patent No.: US 11,103,204 B2
(45) Date of Patent: Aug. 31, 2021

(54) PARALLEL USE OF A MEDICAL X-RAY DEVICE

(71) Applicant: SIEMENS HEATHCARE GMBH, Erlangen (DE)

(72) Inventors: Clemens Joerger, Forchheim (DE); Gudrun Roth-Ganter, Ratshausen (DE)

(73) Assignee: Siemens Healthcare GmbH, Erlangen (DE)

( * ) Notice: Subject to any disclaimer, the term of this patent is extended or adjusted under 35 U.S.C. 154(b) by 301 days.

(21) Appl. No.: 15/378,329

(22) Filed: Dec. 14, 2016

(65) Prior Publication Data

US 2017/0164917 A1    Jun. 15, 2017

(30) Foreign Application Priority Data

Dec. 14, 2015    (DE) .................... 10 2015 225 115.2

(51) Int. Cl.
| | |
|---|---|
| *A61B 6/00* | (2006.01) |
| *G16H 40/20* | (2018.01) |
| *G16H 10/20* | (2018.01) |
| *G16H 30/40* | (2018.01) |
| *G16H 40/63* | (2018.01) |
| *G16H 30/20* | (2018.01) |

(52) U.S. Cl.
CPC ............ *A61B 6/465* (2013.01); *A61B 6/5211* (2013.01); *A61B 6/54* (2013.01); *G16H 10/20* (2018.01); *G16H 30/20* (2018.01); *G16H 30/40* (2018.01); *G16H 40/20* (2018.01); *G16H 40/63* (2018.01)

(58) Field of Classification Search
CPC ......... A61B 6/465; A61B 6/5211; A61B 6/54; A61B 6/548; G06F 19/30; G06F 19/32; G16H 40/63; G16H 40/20; G16H 10/20; G16H 30/20; G16H 30/40
See application file for complete search history.

(56) References Cited

U.S. PATENT DOCUMENTS

| | | | | |
|---|---|---|---|---|
| 6,954,802 B2 * | 10/2005 | Sutherland | ............ | G16H 10/65 710/5 |
| 6,999,558 B2 * | 2/2006 | Okoda | ................ | A61B 6/4233 378/102 |
| 7,218,705 B2 | 5/2007 | Xue et al. | | |
| 7,703,020 B2 * | 4/2010 | Bhattaru | ................ | G16H 30/20 715/740 |

(Continued)

FOREIGN PATENT DOCUMENTS

| | | |
|---|---|---|
| CN | 1541615 A | 11/2004 |
| CN | 1720002 A | 1/2006 |

(Continued)

*Primary Examiner* — Dani Fox
*Assistant Examiner* — Soorena Kefayati
(74) *Attorney, Agent, or Firm* — Laurence A. Greenberg; Werner H. Stemer; Ralph E. Locher

(57) ABSTRACT

A medical X-ray system and a method perform radiological examinations of patients. In order to allow particularly efficient operation of the medial X-ray device, a data processing system of the X-ray system processes data processing processes in parallel and has multiple user interfaces that are used to provide a data input and/or data output option for respective different data processing processes at the same time.

9 Claims, 2 Drawing Sheets

(56) References Cited

U.S. PATENT DOCUMENTS

| | | | | |
|---|---|---|---|---|
| 8,483,461 B2* | 7/2013 | Harvey | A61B 5/055 | 382/130 |
| 9,478,018 B2* | 10/2016 | Rongen | A61B 6/4441 | |
| 2002/0080918 A1* | 6/2002 | Sako | A61B 6/548 | 378/115 |
| 2002/0099571 A1* | 7/2002 | Waku | G16H 40/20 | 705/2 |
| 2004/0028174 A1* | 2/2004 | Koren | G16H 40/67 | 378/4 |
| 2004/0086163 A1* | 5/2004 | Moriyama | A61B 6/566 | 382/131 |
| 2004/0240624 A1* | 12/2004 | Shiibashi | A61B 6/4494 | 378/197 |
| 2005/0002483 A1* | 1/2005 | Wilcox, Jr. | A61B 6/563 | 378/4 |
| 2005/0251006 A1* | 11/2005 | Dellis | G16H 30/20 | 600/407 |
| 2006/0291624 A1* | 12/2006 | Xue | G03B 42/023 | 378/98 |
| 2007/0269017 A1* | 11/2007 | Umeki | A61B 6/00 | 378/165 |
| 2008/0317206 A1* | 12/2008 | Yoshino | G16H 80/00 | 378/98 |
| 2010/0063842 A1* | 3/2010 | Carroll | A61B 6/463 | 705/3 |
| 2010/0080437 A1* | 4/2010 | Yoshida | A61B 6/4464 | 382/132 |
| 2010/0191545 A1* | 7/2010 | Heinert | G16H 30/40 | 705/3 |
| 2010/0223573 A1* | 9/2010 | Tanaka | A61B 6/00 | 715/777 |
| 2010/0305966 A1* | 12/2010 | Coulter | G16H 40/20 | 705/2 |
| 2011/0013220 A1* | 1/2011 | Sabol | G16H 40/67 | 358/1.15 |
| 2011/0081065 A1* | 4/2011 | Canstein | A61B 6/566 | 382/131 |
| 2011/0113329 A1* | 5/2011 | Pusateri | G16H 40/63 | 715/702 |
| 2011/0218427 A1* | 9/2011 | Kitamura | A61B 6/5217 | 600/425 |
| 2011/0311026 A1* | 12/2011 | Lalena | A61B 6/545 | 378/98.5 |
| 2012/0130238 A1* | 5/2012 | Muraoka | A61B 6/507 | 600/436 |
| 2012/0291097 A1* | 11/2012 | Jones | A61B 6/467 | 726/3 |
| 2013/0251106 A1* | 9/2013 | Tajima | A61B 6/542 | 378/62 |
| 2014/0037068 A1* | 2/2014 | Burion | A61B 34/25 | 378/95 |
| 2014/0098931 A1* | 4/2014 | Profio | A61B 6/03 | 378/19 |
| 2014/0136223 A1* | 5/2014 | Phillips | G06Q 10/10 | 705/2 |
| 2014/0155728 A1* | 6/2014 | Lee | A61B 6/467 | 600/407 |
| 2014/0276056 A1* | 9/2014 | Ohta | A61B 8/54 | 600/440 |
| 2014/0304638 A1* | 10/2014 | Yoshikawa | A61B 6/563 | 715/771 |
| 2015/0242586 A1* | 8/2015 | Kagen | G16H 70/60 | 705/2 |
| 2015/0250439 A1* | 9/2015 | Ishii | A61B 6/54 | 378/115 |
| 2015/0272703 A1* | 10/2015 | Arima | A61B 6/465 | 378/62 |
| 2016/0029991 A1* | 2/2016 | Tajima | A61B 6/461 | 378/98 |
| 2016/0143608 A1* | 5/2016 | Schmied | A61B 8/465 | 600/407 |
| 2017/0103552 A1* | 4/2017 | Kim | A61B 5/055 | |
| 2017/0128031 A1* | 5/2017 | Vandenberghe | A61B 6/487 | |
| 2017/0143291 A1* | 5/2017 | Guntzer | A61B 6/542 | |
| 2017/0258449 A1* | 9/2017 | Nielsen | A61B 6/465 | |
| 2017/0303884 A1* | 10/2017 | Takasawa | A61B 6/54 | |
| 2017/0360390 A1* | 12/2017 | Tajima | A61B 6/56 | |

FOREIGN PATENT DOCUMENTS

| | | |
|---|---|---|
| CN | 103607952 A | 2/2014 |
| CN | 103845071 A | 6/2014 |
| DE | 102006029327 A1 | 12/2006 |

* cited by examiner

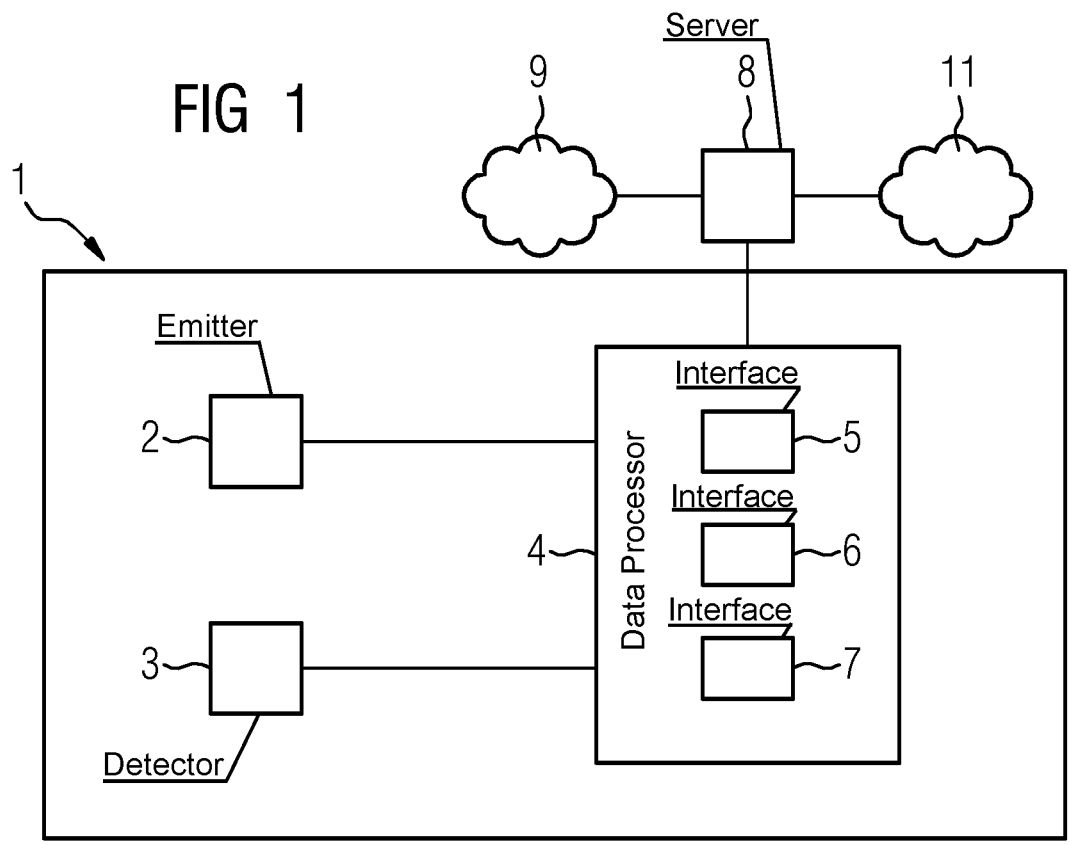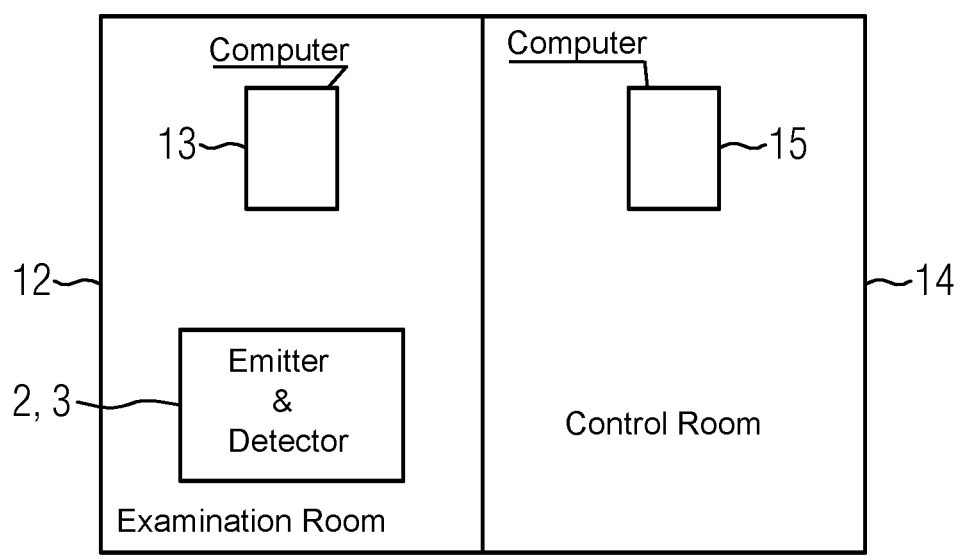

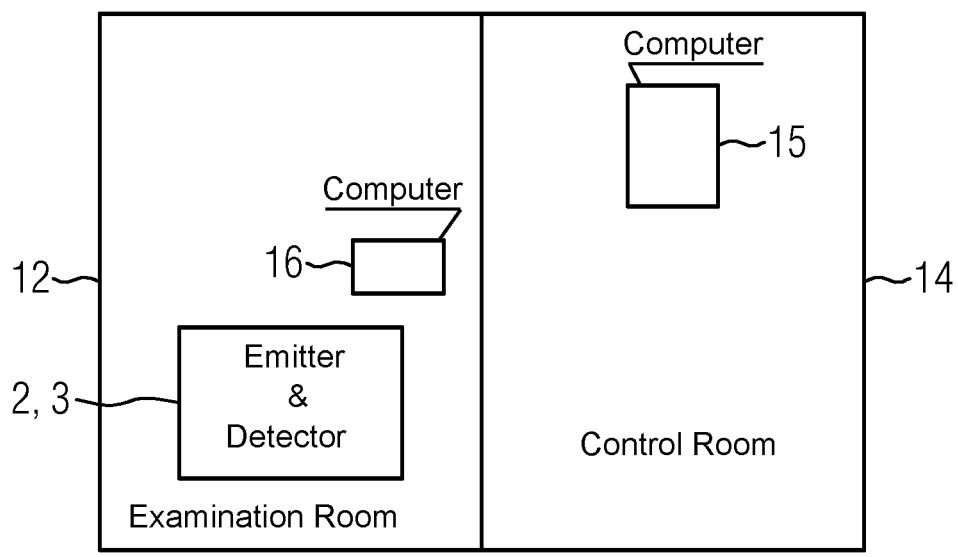
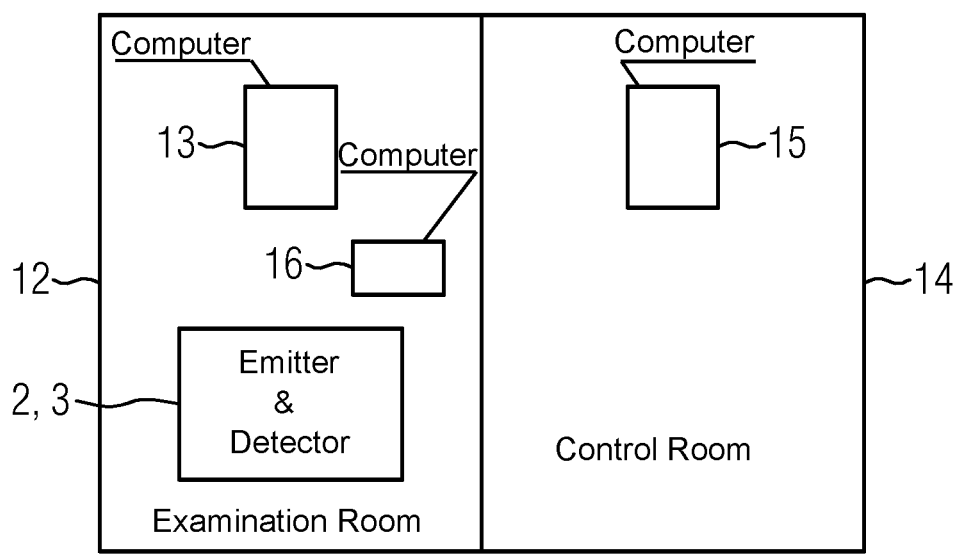

PARALLEL USE OF A MEDICAL X-RAY DEVICE

CROSS-REFERENCE TO RELATED APPLICATION

This application claims the priority, under 35 U.S.C. § 119, of German application DE 10 2015 225 115.2, filed Dec. 14, 2015; the prior application is herewith incorporated by reference in its entirety.

BACKGROUND OF THE INVENTION

Field of the Invention

The invention relates to a medical X-ray device and a method for the radiological examination of patients.

Efficiency and patient flow rate play an ever more important part in radiological examinations, specifically in radiography, where several hundred patients per day can be examined using a machine. The operator would therefore like to perform the necessary work steps, such as patient registration, positioning of the patient, examination, post-processing of the images obtained and archiving, as quickly as possible. Most of these work steps (all except for positioning of the patient) are performed in a digital X-ray system on a computer-aided basis using the image system, which, in most cases today, is implemented by a PC system having a screen, keyboard and mouse.

Hitherto, the cited work steps have been performed by the user in succession. In other words, one patient after the next goes through all of the work steps. Only after the work flow for a patient has concluded completely does the process begin again by executing the first work step for the next patient.

If there are already multiple user interfaces provided as part of the X-ray device, e.g. a first user interface in a control room and a second user interface in an examination room, then these user interfaces are harmonized and display the same work progress for the current patient at the time.

SUMMARY OF THE INVENTION

It is an object of the present invention to allow particularly efficient operation of a medical X-ray device.

Accordingly, the medical X-ray device according to the invention for the radiological examination of patients contains an X-ray emitter and a digital X-ray detector, interacting with the X-ray emitter, for making X-ray recordings and also a data processing system for processing data connected to the radiological examination. The data processing system contains multiple user interfaces that each allow a data input and/or a data output, and is characterized in that the data processing system is configured for parallel processing of data processing processes and uses different user interfaces to provide a data input and/or data output option for respective different data processing processes at the same time and/or uses at least one of the user interfaces to provide data input and/or data output options for different data processing processes at the same time.

The method according to the invention for radiological examination using a medical X-ray system is distinguished in that an X-ray emitter and a digital X-ray detector interacting with the X-ray emitter are used to successively make X-ray recordings for multiple patients, and in that a data processing system is used to process data connected to the making of the X-ray recordings. The data processing system contains multiple user interfaces that each allow at least one data input and/or data output, and is characterized in that the data processing system processes data processing processes in parallel and uses different user interfaces to provide a data input and/or data output option for respective different data processing processes at the same time and/or uses at least one of the user interfaces to provide data input and/or data output options for different data processing processes at the same time.

Advantageous embodiments of the invention are specified in the subclaims.

The advantages and configurations explained below in connection with the X-ray device also apply mutatis mutandis to the method according to the invention and the computer program according to the invention, and vice versa.

A core idea of the invention is to parallel size the work flow for radiological examinations by means of medical X-ray devices. This allows two or three patients to be worked on at the same time. Such parallel working allows particularly effective use of space. Unproductive waiting times can be reduced, since it is no longer necessary to wait for the whole work flow to conclude, but instead it is possible for multiple patients to be worked on in parallel at the same time. In a particularly preferred embodiment of the invention, the use of nonfixed, mobile user interfaces furthermore supports the opportunity for parallel working in an advantageous manner. Depending on the progress of the work flow, a user can perform the respective current work step using a suitable user interface either in the control room or else in the examination room.

During the radiological work flow, which, in the case of X-ray devices known from the prior art, always had to be concluded completely for one patient first before the same work flow begins again for the next patient. The invention proposes that partly overlapping, parallel execution of individual steps of the work flow takes place.

For this, it is firstly necessary to ensure that the processes assigned to different patients are always carried out in proper isolation from one another. To this end, the data processing system used has sufficient memory and computation capacity, particularly for implementing genuine multiprocessing. At the same time, the necessary data integrity needs to be assured for the parallel handling of the processes.

Secondly, the display information made available to the users by the user interfaces must always be in a form such that two things are clearly and explicitly identifiable at any time. First, the display presented to the user must always reveal whether parallel handling is currently taking place, that is say whether the current display relates to the current, examined patient (normal case) or whether the current display relates to finishing of the previous patient or else to preparation of the future patient, and secondly, if parallel handling is taking place, it is necessary to display to the user the work step and the patient to which the current display can be attributed. Only in this way is it possible to reliably avoid confusion.

One way of technically implementing the parallel processing of the processes is starting multiple instances of the image system in the data processing system. In this case, all instances access the same database, e.g. the patients scheduled for examination that are provided as a list by an RIS system.

For safety reasons, there is furthermore provision for the interface in the examination room to always be assigned to the X-ray image of the examined patient. The presentation of the current X-ray image cannot be removed from the display that is in the examination room. An additional display of a further instance of the image system or of another process is possible in the examination room, on the other hand. This other process may also be an instance of the RIS or HIS system, for example.

When a medical engineering assistant uses an X-ray machine, he needs to perform not only operator control of the X-ray machine but also functions on the radiology information system (RIS) or the hospital information system (HIS).

Examples of inputs or interactions with the RIS/HIS system are:
a) viewing or editing a patient questionnaire, e.g. regarding a possible contrast agent allergy or pregnancy of the patient (RIS function),
b) the patient subsequently signing the patient questionnaire, particularly using a user interface, installed on a tablet computer, in the examination room (RIS function),
c) entering a progress for the X-ray examination or else entering general observations concerning the examination (RIS function), and
d) requesting services in a hospital, e.g. requesting an ambulance service (HIS function).

By way of example, details that the patient has forgotten during admission to radiology can be filled in on a patient questionnaire subsequently. If the health situation of the patient so requires, transport can be requested directly from the image system. Conspicuous features during the examination, for example details regarding the motivation of the patient during the examination, details regarding the duration of the examination or the need for follow-up admission, can be input directly into the RIS/HIS system. It is quite particularly advantageous that all inputs on the basis of discontinuation of the necessary work flow can be made independently of the actual X-ray examination of the relevant patient from the point of view of time, that is to say including subsequently and/or for multiple patients at the same time, for example.

While the known X-ray systems have access not only to the control console of the X-ray machine in the control room but additionally to a workstation for the RIS or HIS system, which workstation requires a separate login and has a separate specific user interface, the invention proposes integrating the RIS/HIS functions that are necessary from the X-ray room into the X-ray machine.

Preferably, this is accomplished by virtue of an appropriate RIS/HIS client being provided by the image system. When required, the user uses a suitable action to open a separate window on the screen in which the client runs. An additional RIS/HIS workstation in the control room is then no longer necessary. Changing monitors is dispensed with. The space saved as a result can be used otherwise.

In this connection, a particular advantage is also the particularly flexible and fast input of information to the RIS or HIS system, particularly in emergencies.

The RIS or HIS system can be accessed from any screen workstation or from any mobile computer on which a suitable user interface is provided for data input or data output, i.e. both from the control room and from the examination room. Furthermore, this access can also be effected at any time, i.e. independently of the actual X-ray examination of the relevant patient, that is to say also during preparation of the X-ray recording or during concluding of the X-ray recording or at any interval of time regardless of the time of the X-ray recording, for example. In particular, the invention provides for the data processing system to be configured to process data connected to the X-ray recordings, particularly also to control the X-ray device. In other words, the user interfaces of the data processing system are preferably control consoles of the X-ray device.

The data input option on a user interface is provided by a suitable data input apparatus, for example a keyboard or mouse. Data input can alternatively be effected as a voice input using a microphone or else using a virtual graphical user interface, for example with the aid of a touch-screen.

Data output is accomplished using a suitable output apparatus. This is particularly suitable for presenting a medical image. The output apparatus is therefore preferably a screen, for example the screen of a fixed computer workstation or the screen of a portable computer device.

The fact that the data input and/or output options are provided for respective different processes using different user interfaces at the same time does not just mean that multiple users of the data processing system can use the system at the same time. It particularly also means that parallel handling of different processes at the same time using respective adapted data input and data output apparatuses, for example appropriately adapted user interfaces, can be effected at the same time. The processes processed in parallel, preferably genuinely at the same time, may be either processes directly connected to the X-ray recording, such as preparation of making of and/or follow-up for the X-ray recording, for example, or processes not directly connected to the X-ray recording, such as communication with the RIS or HIS system, for example.

To implement this functionality, the data processing system preferably contains a control unit for controlling the functions of the data input apparatuses and/or of the data output apparatus of the user interfaces, particularly for changing over selected user interfaces from a single mode, in which all interfaces are used to provide the same interface functionality, to a parallel mode, in which different interfaces are used to provide different interface functionalities and/or one interface is used to provide multiple functionalities, and back.

When different user interfaces are used to implement different functionalities, a first user interface can be used for a data input or data output for a first patient, for example, while at the same time a second user interface can be used for a data input or a data output for a second patient. This allows multiple users to use the data processing system at the same time, each individual user using an instance of the respectively called process processed by the data processing system. Alternatively or else in combination therewith, it is possible for a user to use a user interface to use multiple instances of the same process that are associated with the respective patient. If a separate instance of the process is thus started for each patient, then one or more users can use one or more user interfaces to handle different work steps, such as preparation of, making of and follow-up for the X-ray recording, for patients individually in parallel and at the same time.

At the same time, it is possible for a user interface to have a data input or data output option for a further process that is likewise processed at the same time by the data processing system, this further process being a process for direct communication with an RIS or HIS system. In this case, the communication between the data processing system of the X-ray device and the RIS or HIS system can be effected using a DICOM or HL7 connection, and/or the process processed by the data processing system is an RIS or HIS client. Preferably, a virtual machine is provided for execution of the RIS/HIS client by the data processing system. This allows different RIS/HIS clients preferred by the user to be implemented in a simple manner.

The invention can be used on arbitrary radiological systems, for example on fluoro, uro or angio systems.

The method according to the invention can have essential parts performed in a computer-aided manner. The apparatus suitable for performing the method according to the invention can therefore be implemented essentially by providing a suitable data processing system having suitable user interfaces and an appropriately modified piece of operating software.

Insofar as the invention is implemented by using a computer program that contains program instructions that are configured to perform the method when the computer program is executed in the data processing system, particularly in the control unit of the X-ray apparatus. The program instructions are implemented in an arbitrary programming language in a manner known per se and can be provided for the data processing system arbitrary form, for example in the form of data packets that are transmitted via a computer network, or in the form of a computer program stored on a floppy disk, on a CD-ROM or on another data storage medium.

Other features which are considered as characteristic for the invention are set forth in the appended claims.

Although the invention is illustrated and described herein as embodied in a parallel use of a medical X-ray device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is an illustration showing the most important components of an X-ray device according to the invention;

FIG. 2 is an illustration showing a first function assignment for user interfaces;

FIG. 3 is an illustration showing a second function assignment for the user interfaces; and FIG. 4 is an illustration showing a third function assignment for the user interfaces.

DETAILED DESCRIPTION OF THE INVENTION

All of the figures show the invention merely schematically and with its essential constituent parts. The same reference symbols correspond to elements having the same or comparable function in this case.

Referring now to the figures of the drawings in detail and first, particularly to FIG. 1 thereof, there is shown an X-ray device 1 in one exemplary embodiment of the invention which contains an X-ray emitter 2 and a digital X-ray detector 3 interacting with the X-ray emitter 2 in a known manner. Both components are connected via control and data lines to a data processing system 4 of the X-ray device 1, which data processing system has at least one processor for executing program means. The data processing system 4 is used not only to implement a control unit for actuating the X-ray emitter 2 but also to realize an image system that is configured to process and present the digital image signals of the X-ray detector 3. The image system is used to process data in connection with the preparation of, making of and/or follow-up for the X-ray recordings. All functions provided by the data processing system 4 are implemented by hardware and/or software modules. The digital X-ray detector 3 transmits the image data to the image system via a suitable interface, e.g. LAN or WLAN.

By way of example, the data processing system 4 contains three user interfaces 5, 6, 7 in the form of fixed or portable computers. Each user interface 5, 6, 7 has data input apparatuses and data output apparatuses, such as a graphical user interface that is shown on a screen, for example. The data processing system 4 preferably contains a suitable window circuit for windowed presentation of the input and output options, particularly of the graphical user interfaces.

The image system provided by the data processing system 4 is connected to the hospital network, to be more precise to an RIS system 9 and HIS system 11, via an external server 8. The image system is therefore not used just for visualizing the digital X-ray data but rather is also configured such that it is used as an interface in order to connect the X-ray device 1 to the outside world (RIS, HIS, PACS, etc.).

Various cases of parallel use of the X-ray device 1 are outlined by way of example below.

In a first case (FIG. 2), a fixed screen workstation in the form of a computer 13 is located in an examination room 12, together with the X-ray machine having X-ray emitter 2 and X-ray detector 3, the screen workstation being in the form of a control console for the X-ray device 1. The computer 13 is used as a first user interface 5. The image system is executed on the computer 13 in an examination mode, the examination mode relating to the patient currently being examined in the examination room 12. If this examination takes a relatively long time, for example on account of an intervention or else difficult patient repositioning, a second user in a control room 14 adjacent to the examination room can perform the post-processing of the X-ray recordings of the previous patient. For this purpose, a further fixed screen workstation in the form of a computer 15 is provided in the control room 14, the screen workstation being in the form of a control console for the X-ray device 1 and having the image system executed on it in post-processing mode. The computer 15 is used as a second user interface 6. The relevant data input and output options in the control room 14 are changed over specifically for this purpose by an appropriate command from the control unit, whereas this changeover does not take place in the examination room 12. For safety reasons, however, the image from the examination room 12 is shown in the control room 14 in an additional window on the monitor of the computer 15. After the examination of the current patient in the examination room 12 has concluded, the displays in the examination room 12 and the control room 14 are harmonized again.

In a second case (FIG. 3), the current patient in the examination room 12 is X-rayed. The X-ray device 1 is operated from the control room 14. The clinical images are displayed in the control room 14. On the control console therein, the computer 15, the image system is executed in examination mode. During the recording, the next patient is prepared. The preparation of the next patient, e.g. loading the previous recordings, selecting and adapting an appropriate organ program, etc., is performed using a portable computer 16, in this case using a tablet computer, for example. The portable computer 16 is used as a third user interface 7. When the examination carried out by the control room 14 has concluded, the parallel processing is terminated and the patient who has just been prepared on the tablet computer 16 becomes the patient to be examined. The next patient can also be prepared using the tablet computer 16 in the examination room 12 after the X-ray recording has been made, for example, however, for example when the follow-up for the examination takes place, that is to say, by way of example, particular images are selected and sent to the archive, or the requisite documentation is produced for the examination performed, on the computer 15 in the control room 14 using an appropriately adapted user interface.

In a third case (FIG. 4), the two cases outlined above are combined with one another. Both in the control room 14 and in the examination room 12, there are fixed computers 13, 15 on which the image system is executed. A tablet computer 16 is used in the examination room 12 as additional operator control for the image system. While the image system in the examination room 12 runs in examination mode for the current patient, the image system in the control room 14 operates in post-processing mode for the previous patient. The image system that can be operated using the tablet computer 16 is used to prepare the next patient at the same time.

In all three cited cases, a user interface may be configured such that an additional window of the control consoles 13, 15 and/or of the tablet computer 16 is used to display an RIS or HIS client, so that the user can make inputs into the RIS/HIS system 9, 11 directly and immediately and can retrieve and display data provided therefrom.

The outlined cases are distinguished in that different user interfaces 5, 6, 7 are used in this case to effect a data input and/or data output for respective different patients at the same time. By way of example, a first patient is examined and data of a second patient are finished at the same time. Alternatively, it is possible for a data input and/or data output to be effected using at least one of the user interfaces 5, 6, 7 for different patients at the same time. By way of example, a computer 13, 15, 16 can thus be used to examine a first patient and to make an input into the RIS or HIS system for a different patient at the same time.

Although the invention has been illustrated and described in more detail by means of the preferred exemplary embodiment, the invention is not restricted to the examples disclosed and other variations can be derived therefrom by a person skilled in the art without departing from the scope of protection of the invention.

The following is a summary list of reference numerals and the corresponding structure used in the above description of the invention:
1 X-ray device
2 X-ray emitter
3 X-ray detector
4 Data processing system
5 First user interface
6 Second user interface
7 Third user interface
8 Server
9 RIS system
10 (unassigned)
11 HIS system
12 Examination room
13 Fixed computer, control console
14 Control room
15 Fixed computer, control console
16 Portable computer, tablet

The invention claimed is:

1. A medical X-ray device for radiological examination of patients, the medical X-ray device comprising:
an X-ray emitter;
a digital X-ray detector interacting with said X-ray emitter for making X-ray recordings;
a data processing system for processing data connected to the radiological examination, said data processing system having multiple user interfaces each providing at least one data input option and at least one data output option, each user interface of said multiple user interfaces including at least one data input apparatus and at least one data output apparatus including a graphical user interface on a screen, and each said user interface executing an image system configured to process and present digital image signals of said digital X-ray detector, said data processing system configured for parallel processing of data processing processes, said data processing system:
uses different said user interfaces to provide a data input option and a data output option for respective different data processing processes at a same time; or
uses at least one of said user interfaces to provide data input options and data output options for the different data processing processes at a same time;
said data processing system being further configured to implement a control unit for actuating the X-ray emitter; and
said data processing system being configured such that at least one of said user interfaces can be used for a direct data input and/or data output into and/or from a radiology information system (RIS system) and/or a hospital information system (HIS system), for which purpose said data processing system is connectable to said RIS system and/or said HIS system and for which purpose said data processing system provides a virtual machine for executing an RIS or HIS client.

2. The medical X-ray device according to claim 1, wherein at least one of said user interfaces of said data processing system is a first fixed computer disposed in a control room and at least one further of said user interfaces of said data processing system is a second fixed computer disposed in an examination room, which is separate from the control room, or by a portable computer.

3. The medical X-ray device according to claim 1, wherein said data processing system is configured for processing data in connection with a preparation of, making of and/or follow-up for X-ray recordings, and the data input options and the data output options that are providable at the same time relate to the preparation of, the making of and/or the follow up for the X-ray recordings.

4. The medical X-ray device according to claim 1, wherein said data processing system is configured to:
use different ones of said user interfaces to provide the at least one data input option and the at least one data output option for respective different patients at the same time; and/or
use at least one of said user interfaces to provide the data input options and the data output options for the different patients at the same time.

5. A method for radiological examination, comprising the steps of:
successively generating X-ray recordings for multiple patients with an X-ray emitter of a medical X-ray system and a digital X-ray detector interacting with the X-ray emitter;
processing data connected to generation of the X-ray recordings using a data processing system, the data processing system having multiple user interfaces that each allow at least one data input option and at least one data output option, each user interface of the multiple user interfaces including at least one data input apparatus and at least one data output apparatus including a graphical user interface on a screen, and each user interface executing an image system configured to process and present digital image signals of said digital X-ray detector, the data processing system processing data processing processes in parallel, the data processing system performing at least one of the following steps of:
performing respective different data processing processes at a same time using different ones of the user interfaces to provide data input and/or data output; or
performing the respective different data processing processes at the same time using at least one of the user interfaces to provide data input and/or data output;
the data processing system further implementing a control unit for actuating the X-ray emitter; and
the data processing system using at least one of said user interfaces for a direct data input and/or data output into and/or from a radiology information system (RIS system) and/or a hospital information system (HIS system), for which purpose said data processing system is connectable to said RIS system and/or said HIS system and for which purpose said data processing system provides a virtual machine for executing an RIS or HIS client.

6. The method according to claim 5, which further comprises using the different user interfaces to simultaneously perform at least two of the following steps, in each case for different patients:
post-processing of a medical image obtained by virtue of an X-ray recording that has already been made;
operator control of the medical X-ray system to make the X-ray recording and displaying of a medical image obtained by virtue of a current X-ray recording; and
preparing of the medical X-ray system for making a later X-ray recording.

7. The method according to claim 5, which further comprises using at least one of the user interfaces to effect direct access to a radiology information system and/or a hospital information system.

8. The method according to claim 5, which further comprises using at least one of the user interfaces to effect direct access to a radiology information system and/or a hospital information system in order to fill in a patient questionnaire, to request services, or to request an ambulance.

9. A non-transitory computer readable medium comprising instructions, when executed by at least one processor of a control unit of a medical X-ray device, causes the processor to carry out the steps of the method of claim 5.

* * * * *